US010610311B2

(12) United States Patent
Herbelin et al.

(10) Patent No.: US 10,610,311 B2
(45) Date of Patent: Apr. 7, 2020

(54) VIRTUAL REALITY ADD-ON DEVICE FOR STEREOTACTIC NEUROSURGERY

(71) Applicant: ECOLE POLYTECHNIQUE FEDERALE DE LAUSANNE (EPFL), Lausanne (CH)

(72) Inventors: Bruno Herbelin, Ferney-Voltaire (FR); Olaf Blanke, Nyon (CH); Fabien Moreillon, Carouge (CH); Philippe Passeraub, Romont (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 164 days.

(21) Appl. No.: 15/835,650

(22) Filed: Dec. 8, 2017

(65) Prior Publication Data

US 2019/0175284 A1 Jun. 13, 2019

(51) Int. Cl.
| | |
|---|---|
| *A61B 34/00* | (2016.01) |
| *G06F 3/01* | (2006.01) |
| *A61B 90/10* | (2016.01) |
| *A61B 34/20* | (2016.01) |
| *A61B 90/00* | (2016.01) |
| *A61N 1/05* | (2006.01) |
| *G06T 19/00* | (2011.01) |
| *A61B 17/00* | (2006.01) |

(52) U.S. Cl.
CPC .............. *A61B 34/25* (2016.02); *A61B 34/20* (2016.02); *A61B 90/10* (2016.02); *A61B 90/361* (2016.02); *A61N 1/0529* (2013.01); *A61N 1/0534* (2013.01); *G06F 3/011* (2013.01); *A61B 2017/00477* (2013.01); *A61B 2090/365* (2016.02); *G06T 19/006* (2013.01)

(58) Field of Classification Search
CPC ......... A61B 34/25; A61B 34/20; A61B 90/10; A61B 2017/00477; A61B 2090/365; A61B 90/361; A61B 2017/00216; G06F 3/011; A61N 1/0529; A61N 1/0534; G06T 19/006
See application file for complete search history.

(56) References Cited

U.S. PATENT DOCUMENTS

| | | | |
|---|---|---|---|
| 6,283,977 B1 | 9/2001 | Ericsson et al. | |
| 7,313,430 B2 * | 12/2007 | Urquhart ................ | A61B 90/14 600/424 |
| 7,846,116 B2 | 12/2010 | Arn | |
| 2014/0005484 A1 * | 1/2014 | Charles .................. | A61B 17/02 600/201 |
| 2014/0133715 A1 * | 5/2014 | Ballard .............. | G06K 9/00013 382/124 |

(Continued)

*Primary Examiner* — Catherine M Voorhees
(74) *Attorney, Agent, or Firm* — Andre Roland S.A.; Nikolaus Schibli

(57) ABSTRACT

An add-on device for use in combination with a stereotactic apparatus is herein disclosed, the device including a stereotactic adapter, an optical support comprising lenses and a display support adapted to accommodate a virtual reality display. The stereotactic adapter can adapt to different commercial models of stereotactic systems, and is particularly intended for implementing a method for conducting cognitive and/or behavioral tests in subjects during neurosurgery, wherein a virtual reality stimulus is provided to said subject during awake phases of neurosurgery.

14 Claims, 4 Drawing Sheets

(56) References Cited

U.S. PATENT DOCUMENTS

2016/0116742 A1\* 4/2016 Wei .................... G02B 27/0172
                                                            345/156
2018/0042544 A1\* 2/2018 Graham .................... A61B 5/16
2018/0344413 A1\* 12/2018 Rappel ................... A61B 34/00

\* cited by examiner

VIRTUAL REALITY ADD-ON DEVICE FOR STEREOTACTIC NEUROSURGERY

FIELD OF THE INVENTION

The invention related to the field of medical devices for neurosurgery. In particular, the invention concerns an apparatus for the combination of stereotactic neurosurgery with virtual reality approaches.

BACKGROUND

Stereotactic surgery, or stereotaxy, is a minimally invasive form of surgical intervention which makes use of a three-dimensional coordinate system to locate small targets inside the body and to perform on them some action such as ablation, biopsy, lesion, injection, stimulation, implantation or radiosurgery (SRS).

Neurosurgeries are usually conducted under general anaesthesia, but in some cases the patient is awaken during surgery to perform live tests that guide the surgeon during the operation. This is for instance becoming a routine procedure during the implantation of Deep-Brain Stimulators (DBS) for the treatment of essential tremor (ET) and Parkinson Disease (PD). In this procedure, one or more electrodes are placed in deep structures of the brain according to a preliminary localization performed with brain imaging. However, a final check is performed during the surgery to fine-tune the electrode placement and avoid having to re-operate, a practice which is generally called Intraoperative Brain Mapping. In brief, the patient is awakened for a few minutes and the surgery team monitors the tremors on the arm of the patient that become visible as soon as he is awakened: switching the stimulator on should immediately stop the tremors. Being able to adjust the location of the electrode while observing the direct effect on the tremors has the strong advantage of allowing the most appropriate placement and to ensure a successful operation. The same principle applies for ablation and radiosurgery in order to ensure that critical brain areas for important functions are not damaged, for example motor or speech.

Considering the success of DBS on motor disorders, with over 100 000 patients implanted worldwide in 2013, and based on neurological insight of brain functions, it is currently investigated to apply DBS on patients suffering from cognitive disorders such as depression, Obsessive Compulsive Disorders (OCD), Tourette Syndrome or obesity, as examples among the nineteen (19) disorders currently being studied. In these cases, the neurosurgeon cannot rely on a motor feedback (suppression of motor tremors) to ensure the successful placement and efficacy of implanted electrodes. The examination shall here be cognitive and behavioural and is harder to test, thus it is not currently performed during surgery.

Virtual reality (VR) technologies are known for their ability to test cognition, mood, impulsivity, reaction to stimuli and behaviour, in an ecologically valid simulation context adapted to various neurological conditions. VR can therefore provide the cognitive and behavioural simulations required for some new and future use of stereotactic neurosurgery for high level brain functions. VR could for instance be used to guide the placement of neuro-stimulation electrodes during DBS implantation for cognitive and affective disorders.

What remains to be done is to bring VR simulation for patients inside the operating room during awake stereotactic neurosurgery. In particular, head mounted displays to immerse patients lying on the operating table are not available as of today. Accordingly, in light of these deficiencies of the background art, additional and more sophisticated solutions, devices, and methods for VR for surgical procedures are strongly desired.

SUMMARY

According to one aspect of the present invention, as described hereinafter together with the accompanying drawings and the appended claims, describes a new device is provided that addresses and solves the limitations of the background art solutions concerning stereotactic neurosurgery.

According to another aspect of the present invention, a preferred goal is to provide a device allowing conducting cognitive and behavioural tests with VR in patients during awake phases while undergoing neurosurgery. In particular, a device is presented including a virtual reality display specially engineered for intraoperative use during stereotactic neurosurgery. The device is designed to fit on the metallic frame of a stereotactic apparatus, being the part which is fixed on a head of the patient before neurosurgery, and can be placed and removed quickly and at any time during surgical operations. Preferably, the device is adjustable per patient eye-display distance for focus, shape of patient's head, and adaptable to different commercial stereotactic apparatuses.

Among other applications, the device of the invention can allow validating and fine-tuning the placement of deep-brain stimulation electrodes to treat cognitive disorders, or guiding the neurosurgeon during ablative brain surgery of areas involving important cognitive functions.

According to yet another aspect of the present invention, a device is provided as a stereotactic add-on. Preferably, the device includes a stereotactic adapter adapted to be fixed to a stereotactic apparatus, an optical support comprising optical lenses, and a display support adapted to accommodate a virtual reality display.

In one embodiment, the device further includes a virtual reality display located on or within the display support.

According to still another aspect of the present invention, a stereotactic system is provided, including a stereotactic apparatus operatively connected with the stereotactic add-on device as described. The stereotactic adapter described herein is configured to adapt to different commercial models of stereotactic systems.

According to yet another object of the present invention, a method for conducting cognitive and/or behavioral tests in a subject during neurosurgery is provided. Preferably, the method includes the steps of providing a virtual reality stimulus to the subject during awake phases of neurosurgery through the stereotactic add-on device or the stereotactic system.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

Herein, identical reference numerals are used, where possible, to designate identical elements that are common to the figures. Also, the images are simplified for illustration purposes and may not be depicted to scale.

DETAILED DESCRIPTION OF THE PREFERRED EMBODIMENTS

The present disclosure may be more readily understood by reference to the following detailed description presented in connection with the accompanying figures, which form a part of this disclosure. It is to be understood that this disclosure is not limited to the specific conditions or parameters described and/or shown herein, and that the terminology used herein is for the purpose of describing particular embodiments by way of example only and is not intended to be limiting of the claimed disclosure.

As used herein and in the appended claims, the singular forms "a," "an" and "the" include plural referents unless the context clearly dictates otherwise. Also, the use of "or" means "and/or" unless stated otherwise. Similarly, "comprise," "comprises," "comprising," "include," "includes" and "including" are interchangeable and not intended to be limiting. It is to be further understood that where descriptions of various embodiments use the term "comprising", those skilled in the art would understand that in some specific instances, an embodiment can be alternatively described using language "consisting essentially of" or "consisting of."

Figure 1:
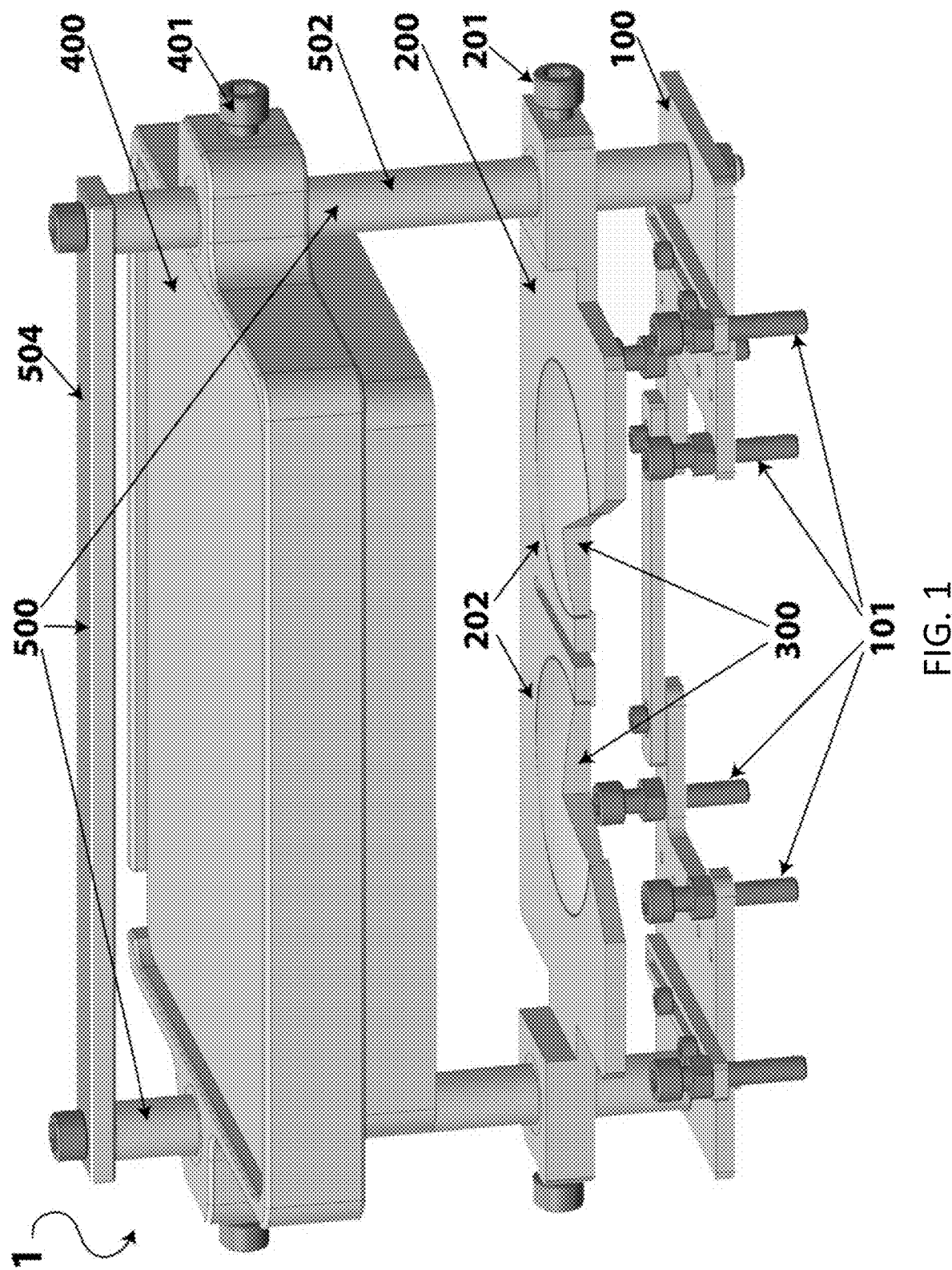
FIG. 1 shows a side perspective schematic view of an embodiment of the device, according to one aspect.
Figure 2A:
FIGS. 2A to 2D shows several photo views of an implemented embodiment of the stereotactic add-on device as well as of a stereotactic system including a stereotactic apparatus operatively connected with the stereotactic add-on device, with FIG. 2A showing a side view of the stereotactic add-on device, FIG. 2B showing a view along the viewing axis, FIG. 2C showing the system from a side perspective view arranged on a stereotactic frame (Elekta Leksell) as it would be on a patient, and FIG. 2D showing another view along the viewing axis.
Figure 2B:
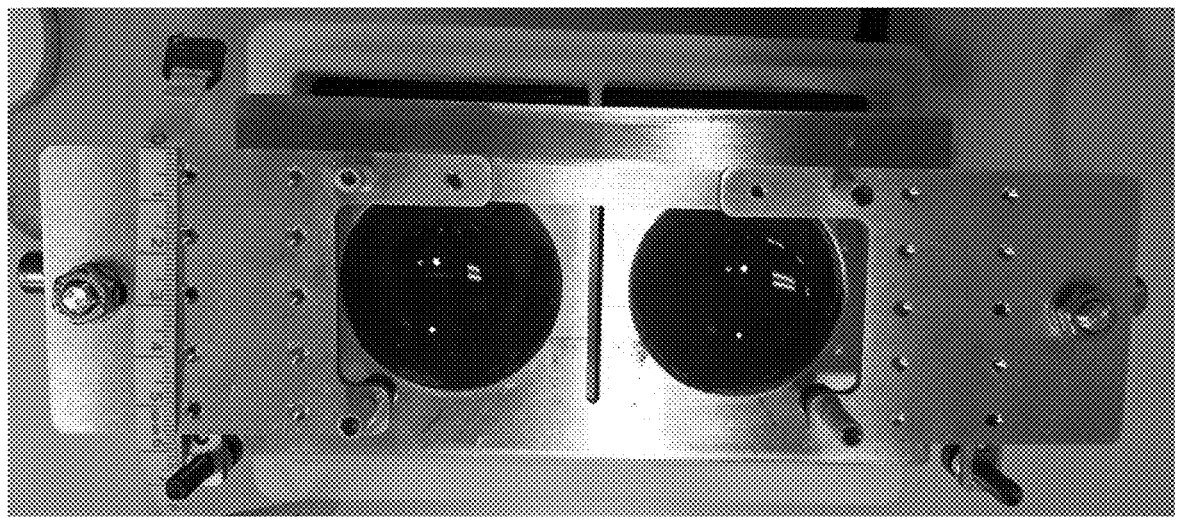
Figure 2C:
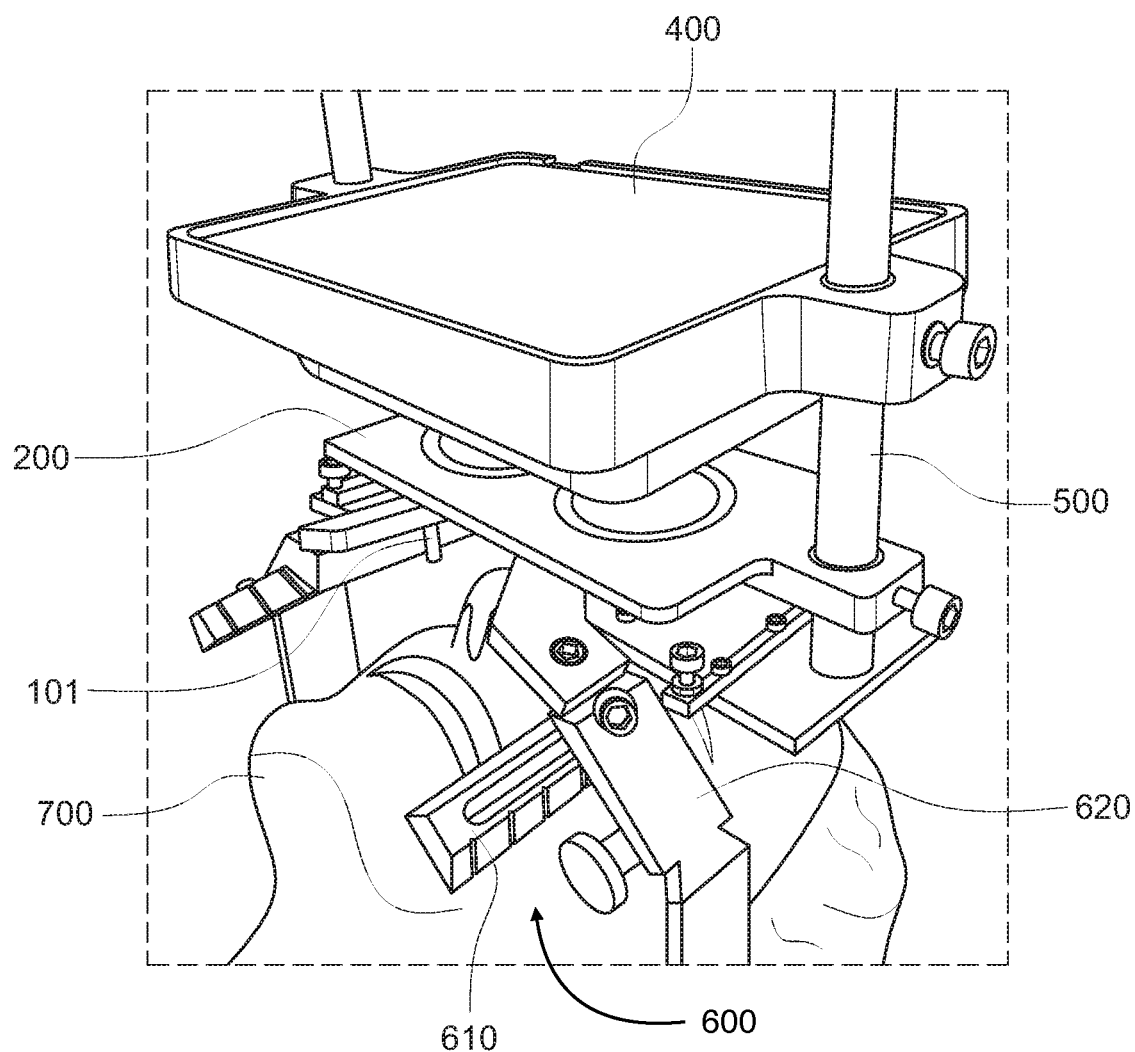
Figure 2D:
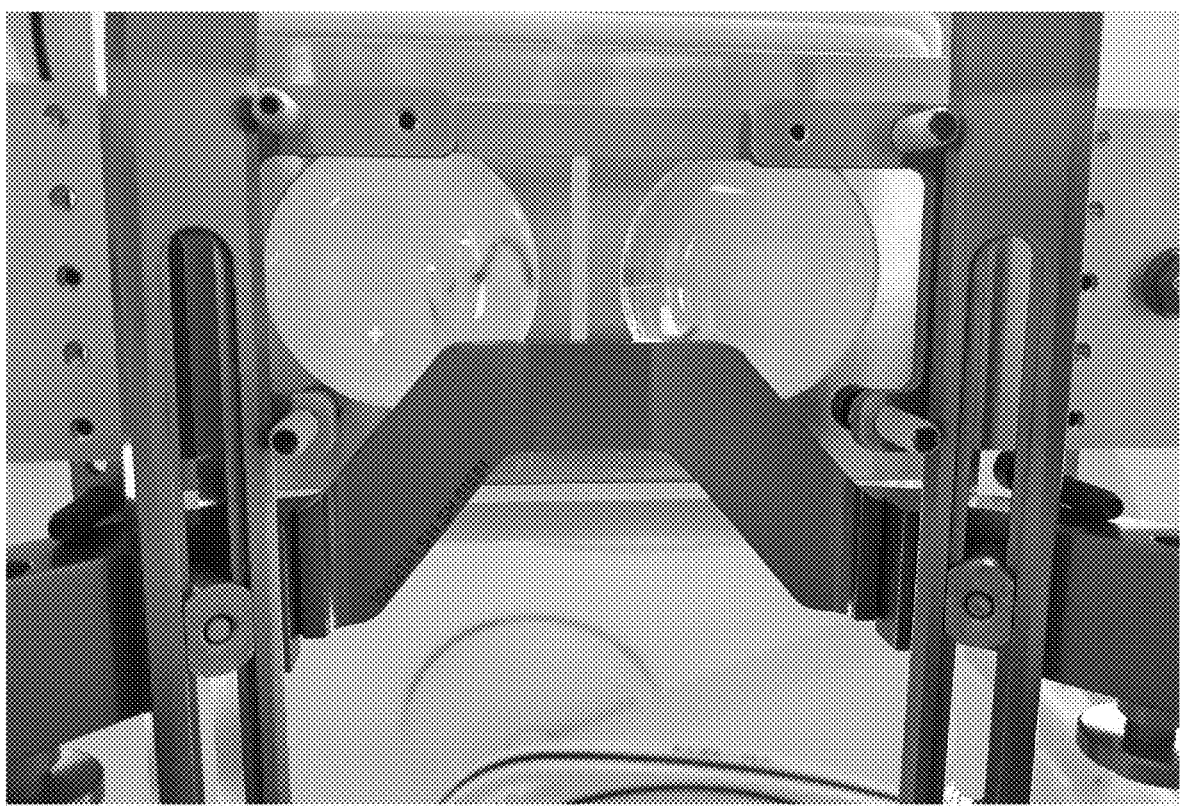

With reference to FIG. 1, a stereotactic add-on device 1 according to one embodiment of the present invention is shown. The device 1 includes three main components operatively connected between them: a stereotactic adapter 100 configured to be fixed to a stereotactic apparatus (not shown), an optical support 200 including optical lenses 300, and a display support 400 adapted to accommodate a virtual reality display. In the shown embodiment, the three main components are designed as plate-like elements having a flat appearance, and are arranged in a parallel fashion between them, i.e. in such a way that their main longitudinal axes run in parallel. In alternative embodiments, the stereotactic adapter 100 can be designed and disposed in a non-parallel fashion compared to optical support 200 and display support 400, as long as these two latter elements remain in a parallel configuration. In still an alternative embodiment, the optical support 200 and display support 400 can have a relative inclination of a certain degree.

However, as it will be evident for a person skilled in the art, according to another aspect of the present invention, one aspect is related to the relative position between the optical support 200, the adapter 100 and the display support 400, which is adapted to facilitate the functional connection between optical lenses 300 and a VR display disposed within the said support 400 when the device in use. The optical support 200 and display support 400 are relatively arranged in such a way that the optical lenses 300 provide to a user the correct VR image when functionally connected with a VR display.

In the frame of the present disclosure, the expression "operatively connected", "operatively connecting" and the like, as well as the expression "functionally connected", "functionally connecting" and the like, reflects a functional relationship between the several components of the device of the invention among them, that is, the term means that the components are correlated in a way to perform a designated function. The "designated function" can change depending on the different components involved in the connection; for instance, the designated function of optical lenses functionally connected to a VR display is the adaptation and correction of a VR image provided on a VR display to be suitable for a user's interpretation. This implies the correct display on the VR display of stereoscopic images (horizontal split for left and right eyes) with geometric distortions compensating for the optical lens distortion.

In preferred embodiments, a frame 500 operatively connects the several components of device 1 among them, so to facilitate e.g. their relative positioning. For example, frame 500 can be made of a transversal bar 504 and two or more rods, bars, or beams 502 that are arranged perpendicularly to the transversal bar 504, the rods, bars, or beams 502 are configured to allow a sliding movement of display support 400, optical support 200 and stereotactic adapter 100 relative to each other. Rods, bars, or beams are arranged to be substantially parallel to the optical axis of the device 1. For example, both display support 400 and optical support 200 can have holding elements that engage with the bars, for example having a round cross-sectional shape, and can be fastened to the bars with screws 201, 401. The stereotactic adapter 100, optical support 200 and display support 400 can be physically fixed to the frame 500 by other means, such as clamps, springs, engagement bolts, glues, etc., or can in some embodiments form part of the frame 500 itself. For instance, in one embodiment, as shown in FIG. 1, the stereotactic adapter 100 forms the bottom part of a frame 500. Preferably, at least one of optical support 200 and display support 400 are movably fixed to frame 500 so to easily adjust the distance between a VR display and the optical lenses 300; for instance, optical support 200 can be slid along a frame 500 by unscrewing screw(s) 201 and adjusted in height until a suitable distance between VR display and the optical lenses 300 is reached. This feature allows to easily adapt the design of device 1 to different types of user and focal distance so that a VR image is conveniently provided to a subject.

Optical lenses 300 are accommodated in any suitable way on or within the optical support 200; for instance, said support 200 can comprise one or more recesses 202 adapted to hold the lenses, which in many advantageous embodiments are two. Lenses 300 used in the frame of the present invention are those commonly used in virtual reality approaches, such as aspheric or Fresnel lenses. The diameter of the lenses 300 is adapted to be large enough to accommodate with different distances between user's eyes, or interpupillary distance, varying slightly from person to person. Alternatively, the distance between the lenses 300 can be adjusted to match a user's interpupillary distance, by e.g. laterally displacing the recesses 202 between them. Lenses 300 are conceived to focus and reshape the pictures usually coming from a VR display for each eye, and to create a stereoscopic 3D image by angling two 2D images to mimic how each of people's two eyes independently view. Lenses 300 can have a magnification usually in the range of 5 to 20×, and a diameter comprised between 20 and 100 mm, such as between 30 and 60 mm.

In some embodiments of the invention, device 1 further comprises a VR display positioned within the display support 400. In an implemented embodiment, a display retrieved from the VR Oculus V1 helmet has been used (1280×800 resolution). As used herein, a "virtual reality display" or "VR display" is a display device adapted to provide a virtual reality image or video. Usually, a VR display has a high resolution (e.g. 1280×800 and above) and the ability to show stereoscopic imagery, and typically has one or two small display units such as cathode ray tubes (CRT), liquid crystal displays (LCDs), liquid crystal on silicon (LCos), or organic light-emitting diodes (OLED) displays. Multiple micro-displays can be used to increase total resolution and field of view. The entire system can comprise further elements adapted to provide e.g. a more realistic, intense and/or immersive VR experience, such as for instance means for eye tracking to measure the point of gaze, allowing a computer device to sense where the user is looking. This information is useful in a variety of contexts such as user interface navigation: by sensing the user's gaze, a computer can change the information displayed on a screen.

The stereotactic adapter 100 is designed to be movably and/or removably adapted to a stereotactic apparatus as many known in the art such as the Elekta Leksell Stereotactic System® and described e.g. in U.S. Pat. Nos. 6,283,977 and 7,846,116, showing devices for fixation of the head, these two references herewith incorporated by reference in their entirety. Adapter 100 can be fixed to a stereotactic apparatus via any suitable means, such as pins 101 designed and positioned along the said support to block the entire add-on device by means of tight adjustment with rubber contact, or even adhesive or magnetic means.

The entire device, except for the optical lenses 300, can be manufactured with such materials, and adapted in its overall shape, to compatibly work and fit with various additional external devices or systems typically used and found in operating rooms and/or in the frame of neurosurgical operations, such as e.g. CT scanner, MR systems or Angiograms.

Another object of the present invention relates to a stereotactic system comprising a stereotactic apparatus operatively connected with the stereotactic add-on device as described. In an implemented, non-limiting embodiment of the system, shown in FIGS. 2A to 2D, the stereotactic add-on device of the invention has been operatively coupled to an Elekta Leksell Stereotactic System® by connecting the stereotactic adapter 100 via pins 101 to a device for fixation of the head 600 as the one described in U.S. Pat. No. 7,846,116. In particular, frame 500 through its stereotactic adapter portion 100 is screwed to two of the four pin support members 610 of the device for fixation of the head 600, at the level of the elongated through slot of the frame part 620 attachment portions thereof. Thanks to this expedient, the stereotactic adapter 100 can be easily adjusted by moving it along the longitudinal direction of the device for fixation of the head 600, and fixed with pins 101 in order to adapt the device 1 to the specific conditions associated with each patient 700.

As it will be evident, one aspect of the present invention relates to the use of the stereotactic add-on device or the stereotactic system as described for conducting cognitive and/or behavioral tests in a subject during awake phases of neurosurgery through virtual reality. A method for performing such tests is also envisaged by the present invention, characterized in particular by the fact of comprising a step of providing a virtual reality stimulus to a subject during awake phases of neurosurgery through the stereotactic add-on device or the stereotactic system of the invention.

In a non-limiting embodiment of this aspect of the invention, the method of the invention foresees an improved procedure and clinical outcomes by combining the possibility of performing cognitive and/or behavioral tests with deep brain stimulation (DBS) in subjects with disorders associated with the brain. As used herein, the term "disorder associated with the brain" and "brain disorder" is meant to encompass all disorders (or symptoms thereof) that originate in the brain or other parts of the body, which can be affected by electrical stimulation of cells or target regions within the brain. For example, studies have associated particular areas of the brain with a variety of conditions including movement-related disorders; disorders with a psychiatric component such as depression, affective disorder, anxiety disorders, bipolar disorder, obsessive compulsive disorder (OCD), manias, phobias, eating and vomiting disorders and the like, for example psychiatric disorders, obesity; memory disorders; and disorders involving pain such as migraines. Accordingly, the method of the present invention can be advantageously used for treating the above-listed disorders, particularly psychiatric ones. As used herein, "treatment", "treating" and the like generally refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease. The effect may be prophylactic in terms of preventing or partially preventing a disease, symptom or condition thereof and/or may be therapeutic in terms of a partial or complete cure of a disease, condition, symptom or adverse effect attributed to the disease.

Also, the term "treatment" as used herein covers any treatment of a disease in a mammal, particularly a human, and includes: (a) preventing the disease from occurring in a subject which may be predisposed to the disease but has not yet been diagnosed as having it for example based on familial history, overweight status or age; (b) inhibiting the disease, i.e., arresting its development; or (c) relieving the disease, i.e., causing regression of the disease and/or its symptoms or conditions such as improvement or remediation of damage.

DBS is an advanced neurosurgical procedure typically performed by a clinical team including neurologists, neurosurgeons, neurophysiologists and other specialists trained in the assessment, treatment and care of neurological conditions. Briefly, following selection of an appropriate patient and determination of the brain region to be targeted, precise placement of an electrode or lead in the patient's brain is carried out in an operating room setting, typically utilizing advanced brain imaging technology and stereotactic targeting.

Lead implantation may take place under local anesthesia or with the patient under general anesthesia ("asleep DBS"). A hole about 14 mm in diameter is drilled in the skull and the probe electrode is inserted stereotactically. During the awake procedure with local anesthesia, feedback from the patient is used to determine the optimal placement of the permanent electrode. During the asleep procedure, intraoperative MIll guidance is used for direct visualization of brain tissue and device. The installation of the IPG and extension leads occurs under general anesthesia.

The use of the stereotactic add-on device or the stereotactic system according to the invention would help neurosurgeons in the above-mentioned awake phase in those scenarios in which e.g. DBS implantation is performed to address psychiatric disorders: during or immediately after implantation and/or activation of the electrode leads, a patient undergoing the surgical procedure could be exposed while awake to virtual reality stimuli adapted and tailored depending on the needs and circumstances. As a way of example, once the patient awake, a DBS could be activated and the patient exposed to an immersive VR scenario in which VR stimuli are provided, those stimuli replicating for instance typical situations reproducing a sense of anxiety, phobia, or triggering targeted behaviour associated to the disorder of the patient. Through these behavioural/cognitive tests, the neurosurgeon would be able to assess the good outcome of the surgery, tailoring the electrical stimulation, better defining the positioning of a DBS electrode and the like.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims

The invention claimed is:

1. A stereotactic add-on device to be fixed to a head fixation device of a stereotactic apparatus comprising:
   a stereotactic adapter having a frame, the stereotactic adapter configured to be fixed to the head fixation device;
   an optical support having a pair of optical lenses attached to the stereotactic adapter; and
   a display support attached to the stereotactic adapter, the display support configured to accommodate a virtual reality display,
   wherein the optical support and the display support are movably fixed to the frame, and
   wherein the frame is configured so that the optical support can slide along the frame to adjust a distance between the display support and the pair of optical lenses.

2. The stereotactic add-on device of claim 1, further comprising:
   a virtual reality display located on or within the display support.

3. The stereotactic add-on device of claim 1, further comprising:
   a fixation device configured to fix a position of the optical support and the display support along the frame.

4. The stereotactic add-on device of claim 1, wherein the frame is configured to be attached to at least one pin support member of the stereotactic apparatus.

5. A stereotactic system comprising a stereotactic apparatus operatively connected with the stereotactic add-on device of claim 1.

6. A method for conducting cognitive and/or behavioral tests in a subject during neurosurgery, comprising the step of providing a virtual reality stimulus to the subject during awake phases of neurosurgery through the stereotactic add-on device of claim 2.

7. The stereotactic add-on device of claim 2, wherein each optical lens is configured to focus and reshape pictures from the virtual reality display for a corresponding eye of a patient to which the head fixation device is affixed to.

8. The stereotactic add-on device of claim 1, wherein each optical lens includes a fresnel lens.

9. The stereotactic add-on device of claim 1, wherein each optical lens includes an aspheric lens.

10. The stereotactic add-on device of claim 1, wherein each optical lens has a magnification in a range between 5× to 20× and a diameter in a range between 20 mm and 100 mm.

11. The stereotactic add-on device of claim 2, wherein the stereotactic adapter and the frame provide for a fixed positional relationship between the optical lenses and the virtual reality display.

12. A stereotactic add-on device to be fixed to a head fixation device of a stereotactic apparatus comprising:
    a stereotactic adapter configured to be fixed to the head fixation device;
    an optical support having a pair of optical lenses attached to the stereotactic adapter;
    a display support attached to the stereotactic adapter, the display support configured to accommodate a virtual reality display; and
    a virtual reality display attached to the display support,
    wherein each optical lens is configured to focus and reshape pictures from the virtual reality display for a corresponding eye of a patient to which the head fixation device is affixed to.

13. A method for conducting cognitive and/or behavioral tests in a subject during neurosurgery, comprising the step of providing a virtual reality stimulus to the subject during awake phases of neurosurgery through the stereotactic add-on device of claim 12.

14. A stereotactic add-on device to be fixed to a head fixation device of a stereotactic apparatus comprising:
    a stereotactic adapter having a frame, the stereotactic adapter configured to be fixed to the head fixation device;
    an optical support having a pair of optical lenses attached to the stereotactic adapter; and
    a display support attached to the stereotactic adapter, the display support configured to accommodate a virtual reality display,
    wherein the optical support and the display support are movably fixed to the frame, and
    wherein the stereotactic adapter and the frame provide for a fixed positional relationship between the optical lenses and the virtual reality display.

* * * * *